(12) United States Patent
Oommen

(10) Patent No.: US 7,959,000 B2
(45) Date of Patent: *Jun. 14, 2011

(54) DEVICE FOR COLLECTION, STORAGE, RETRIEVAL AND SHIPPING OF HAIR FOLLICLES FROM ANIMALS

(75) Inventor: Abraham Oommen, Lincoln, NE (US)

(73) Assignee: Neogen Corporation, Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/054,839

(22) Filed: Mar. 25, 2008

(65) Prior Publication Data

US 2008/0300505 A1  Dec. 4, 2008

Related U.S. Application Data

(63) Continuation of application No. 10/857,669, filed on May 29, 2004, now Pat. No. 7,470,399.

(51) Int. Cl.
*B65D 73/00* (2006.01)
*B65D 81/02* (2006.01)

(52) U.S. Cl. ......... 206/460; 206/438; 206/484; 206/223

(58) Field of Classification Search .................. 206/438, 206/460, 813, 484, 484.1, 484.2, 447, 206, 206/223, 569, 570; 422/61; 15/104.002
See application file for complete search history.

(56) References Cited

U.S. PATENT DOCUMENTS

| | | | |
|---|---|---|---|
| 2,724,847 A | | 11/1955 | Krasno |
| 3,029,453 A | * | 4/1962 | Norman .................. 15/104.002 |
| 3,082,453 A | * | 3/1963 | Mutchler et al. ......... 15/104.002 |
| RE25,435 E | * | 8/1963 | Norman .................... 15/104.002 |
| 3,231,918 A | * | 2/1966 | Marks ...................... 15/104.002 |
| 3,785,930 A | | 1/1974 | Ellis |
| 4,570,797 A | * | 2/1986 | Weinman ...................... 206/447 |
| 4,713,274 A | * | 12/1987 | Minor ........................... 428/40.1 |
| 4,928,814 A | * | 5/1990 | Rondot et al. ................. 206/215 |

(Continued)

FOREIGN PATENT DOCUMENTS

WO  WO 01/18239 A1  3/2001

OTHER PUBLICATIONS

Print out from Genetic Solutions Pty. Ltd. comprising 14 pages, http://www.geneticsolutions.com.au.

*Primary Examiner* — Steven A. Reynolds

(74) *Attorney, Agent, or Firm* — Ian C. McLeod; Steven M. Parks

(57) ABSTRACT

The present invention relates to a novel device for the collection, storage, shipping and retrieval of hair follicles from animals for the purpose of isolating DNA or other genetic material from the follicles for analysis. The device has outer flaps for the protection as well as identification of the samples and an inner part where samples are placed. The inner device has thicker base and a clear plastic cover, the easy peel back of which is facilitated by a) low tack adhesives that hold the two together and b) a touch cut on one end, through the base sheet which creates a grip. This makes the device convenient and easy to use, and yet a robust collection device for hair follicles from animals in a farm or real-life situation. Hair follicles can be punched out through the inner device for direct DNA isolation and analysis.

11 Claims, 3 Drawing Sheets

U.S. PATENT DOCUMENTS

| | | | |
|---|---|---|---|
| 5,496,562 A | 3/1996 | Burgoyne | |
| 5,716,831 A * | 2/1998 | Whalon et al. | 435/19 |
| 5,922,427 A * | 7/1999 | King | 428/40.1 |
| 6,607,699 B1 * | 8/2003 | Elliott et al. | 422/61 |
| 6,632,403 B1 | 10/2003 | Barmore et al. | |
| 6,632,661 B2 * | 10/2003 | Wickert | 435/305.4 |
| 2004/0069673 A1 * | 4/2004 | Dinges | 206/484 |

* cited by examiner

DEVICE FOR COLLECTION, STORAGE, RETRIEVAL AND SHIPPING OF HAIR FOLLICLES FROM ANIMALS

CROSS-REFERENCE TO RELATED APPLICATION

This application is a continuation of and claims the benefit of and priority to U.S. Non-provisional patent application Ser. No. 10/857,669, filed May 29, 2004, now U.S. Pat. No. 7,470,399 issued on Dec. 20, 2008 entitled DEVICE FOR COLLECTION, STORAGE, RETRIEVAL AND SHIPPING OF HAIR FOLLICLES FROM ANIMALS, which document is hereby incorporated by reference to the extent permitted by law.

STATEMENT REGARDING FEDERALLY SPONSORED RESEARCH AND DEVELOPMENT

Not applicable.

BACKGROUND OF THE INVENTION

The rapid growth and development in the area of molecular biology has allowed the development of numerous genetic tests for animals. As the number of useful tests increase, there will be an increase in the number of samples to be tested. Currently, the number of samples that are being sent for DNA analysis are increasing exponentially. Also, the types of samples that are sent for DNA analysis can vary from place to place and organization to organization. In other words, for animals, the source material for DNA can be hair follicles, ear notches or ear punches, blood and meat samples (if the animal is already dead). In all cases, the type of samples will be determined by the individual or the organization collecting the samples. Some ranches that specialize in beef cattle may find it easy to get ear notches when the animals are rounded up for selling or some ranches may find it convenient to collect hair from tail switches when a new calf is born. Whatever the case may be, there is no single, easy to use device that is convenient for field use as well as for laboratory use. A unique and novel device has to work equally well in the field where the sample is collected and has to work equally well in a laboratory where the biological sample is to be isolated and subject to numerous biochemical tests.

No single device or system exists that allow the easy collection, safe storage and shipping as well as the ability to isolate DNA; all combined in one device. In recent years, several approaches have been made to create sample collection kits for human hair (Bierke-Nelson et al, 1999, Elliot et al, 2003). None of the devices or systems used today specifically approaches the issues regarding a) ease of collection of samples, b) ease of identification of samples and c) ability to keep samples for long time and d) ability to isolate DNA through the device so as to get routine amplification of DNA possible. One has to consider the fact that most animal samples are collected in the field and hence the collection device should be sturdy as well as easy to use and without any disposable or removable part or component.

BRIEF DESCRIPTION OF INVENTION

The present invention relates to a novel device for the collection, storage, shipping and retrieval of hair follicles from animals for the purpose of isolating DNA or other genetic material from the follicles for analysis. The device has outer flaps for the protection as well as identification of the samples and an inner part where samples are placed on low tack adhesives. The low tack adhesive component allows peeling of a clear plastic cover which allows visibility of the sample once placed inside and the easy peeling of the plastic cover is facilitated by a touch cut that is one of the uniqueness of this device. The ease of peeling the clear sheet along with the ability to hold the entire device with the outer flaps makes it a convenient and easy to use, yet robust collection device for hair follicles from animals in a farm or real-life situation.

BRIEF DESCRIPTION OF THE SEVERAL VIEWS OF THE DRAWINGS

There are 3 figures labeled FIG. 1, FIG. 2 and FIG. 3. None of the figures are drawn to scale. The figures are for the purpose of showing details of the device and its functionality.

DETAILED DESCRIPTION OF THE INVENTION

The present invention provides a unique device for collecting biological samples from animals and allowing proper identification, long-term storage, shipping as well as the ability to easily isolate genetic material from the biological sample.

Figure 1:
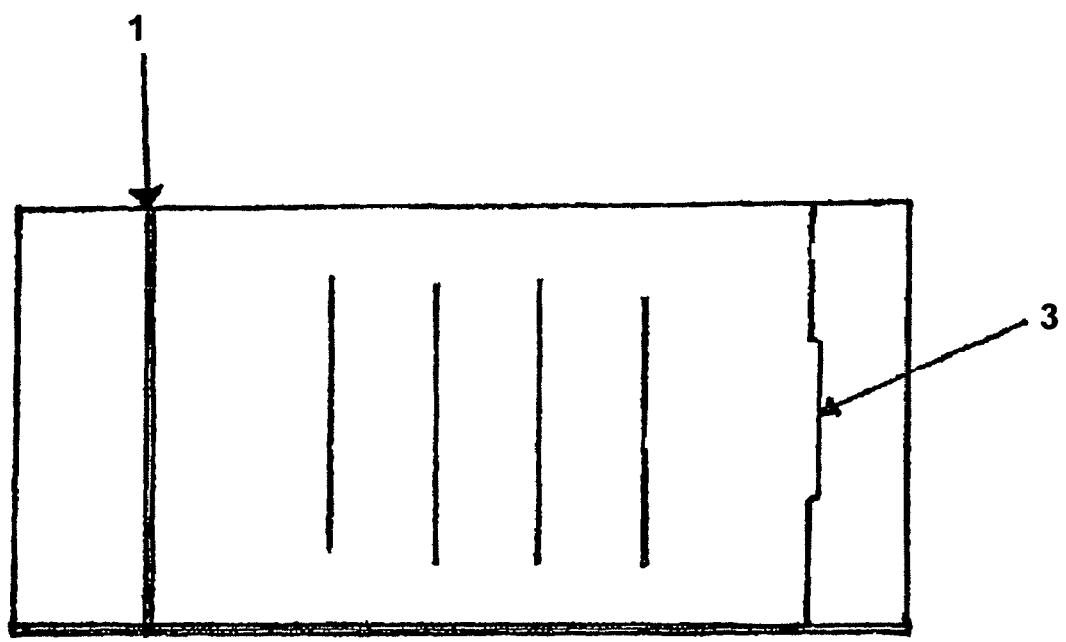
FIG. 1. Lateral view of the device. The closed device is shown with the external cover flap as viewed from the top. The arrow indicated as (3) shows the tab that is on the top outer flap inserted into the bottom outer flap through a slit on the bottom flap. The arrow indicated as (1) shows the fold crease that allows the outer flaps to be folded. The outer flap also has areas to write useful information about the sample like Name, Animal ID, Signature of submitting person, date etc. The back of the device (back of bottom flap) typically has a unique barcode that is used to identify each device.
Figure 2:
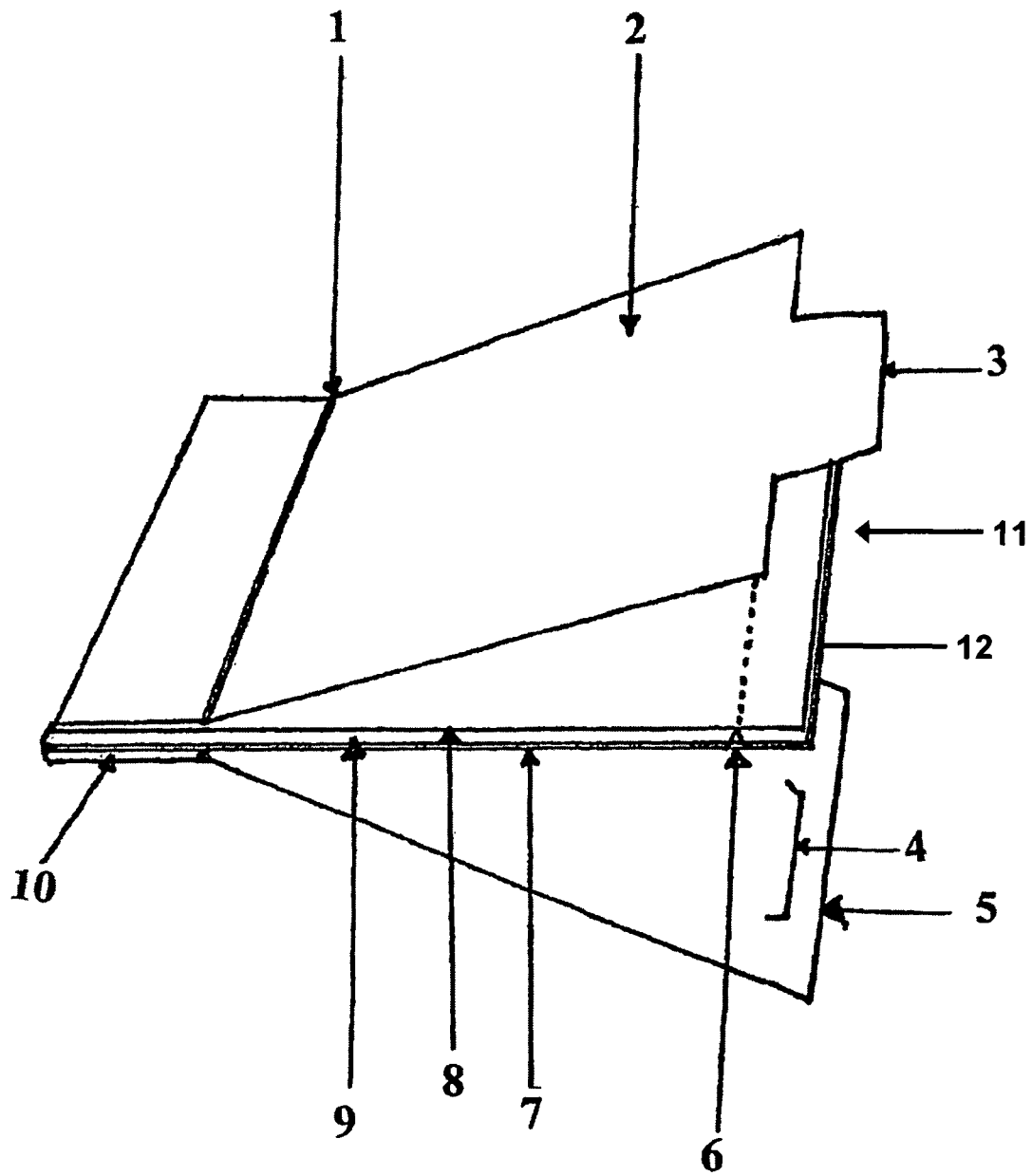
FIG. 2. Open view of device showing outer flaps and inner device. The open device shows outer flaps (2) and (5) that are open exposing the inner device (11) which is attached to the outer flaps (2), (5) with glue in the general area that is marked with arrow (10) (e.g., to secure entire device as one unit). The folded crease (1) is found on the top (2) and bottom (5) outer flaps and allows opening of the protective outer flaps (2), (5). The inner device (11) has a lower base sheet which is indicated by arrow marked (7). The lower base sheet (7) is slightly thicker than the upper clear plastic which is indicated by arrow marked (8). The two sheets (7), (8) are layered on each other using low tack adhesives, the concept of which is indicated by arrow marked (9). The lower base sheet (7) of the inner device (11) is cut using a touch cut device and this cut stops at the upper clear plastic sheet (8). The cut is indicated by arrow marked (6). The cut completely cuts the lower base sheet (7) but does not cut the upper clear plastic sheet (8). This allows the use of the cut area in which part of the lower base sheet (7) is attached to the clear plastic sheet (8) as a grip (12) to peel the clear plastic sheet (8) back. Since low tack glue is used, the plastic sheet (8) can be peeled back and re-attached at will. To close device after putting a sample in the inner device (11), the whole unit is pressed together by hand and tab (3) is inserted to slit (4) which will hold all contents securely.
Figure 3:
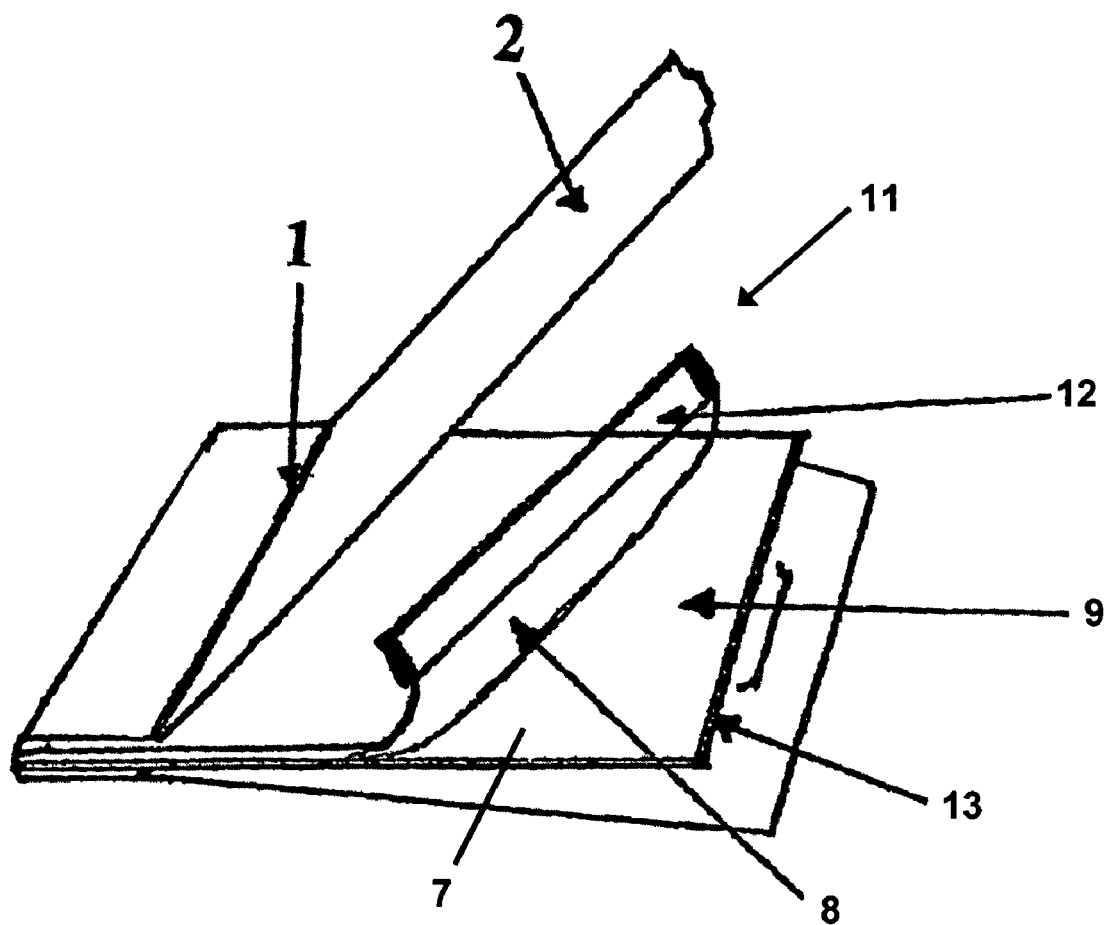
FIG. 3. Open inner device. This figure shows open flaps using the folding crease as indicated by arrow marked (1). The inner device (11) is shown, with the clear plastic that is indicated by arrow marked (8), being peeled back from the lower base sheet(7). This exposes the low tack adhesive as indicated by arrow marked (9). Hair follicles can be placed in between the clear plastic sheet (8) and the lower base sheet (7) and secured by placing the clear plastic sheet (8) back on top of the sample and then closing the entire device. The touch cut (6) creates a grip (12) on the upper clear plastic sheet (8) by leaving a part of the lower base sheet (7) as indicated by arrow marked (12). The touch cut (6) is now exposed as the edge of the lower base sheet (7) and this is indicated by arrow marked (13).

The basic design is described in FIG. 1. The details of the device is derived from FIG. 2 and the use of the device can be inferred from FIG. 3. The entire device is about the size of a standard business card. The size can be varied to fit any requirement. There are two paper flaps that can be opened by a fold created in the paper and also by attaching the paper using glue or any other adhesive. The device has a folding crease close to the main fold that allows the user to hold the device in one hand which allows easy separation of the paper flaps with the other. The two paper flaps are outer covers that protect the biological sample that is to be placed within a specialized part that is within the two flaps. The two outer flaps are used also to identify the source of the material and has adequate room for basic sample information like name of the animal, animal ID, date and signature of submitting individual. On the outside or inside of the outer flaps is sufficient space for instruction. In most cases, the outside of the lower flap is used to print a unique barcode that identifies each device. The outer paper can be card stock or similar paper so that the device is sturdy and can be used in the field. In the present embodiment, the inside device (protected by the two outer flaps) is a clear plastic sheet that is placed on a paper or plastic base that is white or any other color that allows easy recognition of hair follicles, once the hair follicles are inside the device. The paper or plastic base is made of slightly heavier material than the outer clear plastic so that it can act as a base. The inner device is attached to the outer device using adhesives placed close to the folded area of the outer cover. This is indicated in FIG. 2 and marked by arrow (10). The clear plastic top allows easy visualization of hair follicles once it is placed in the device by the person collecting the samples, as well as personnel in a laboratory who might be using the follicles to isolate DNA. The clear plastic top sheet is layered on the base sheet using low tack adhesive that allows easy peeling back of the clear plastic sheet as well as easy re-closing. Such a paper combination with low tack adhesives can be found as off the shelf product from graphic film suppliers. A touch cut on the edge of the base sheet (edge away from the attached area) allows for easy peel back of the clear plastic sheet due to the low tack adhesive. A touch cut is a machine derived cut that slices to set depth and in this case, cuts deep enough so as to cut the base sheet only and not the clear plastic. The clear plastic sheet cannot be completely peeled off the base sheet since the entire inner device is attached to the outer cover thus allowing for an environmentally friendly device which does not have any removable component.

Using the Device

The present embodiment is primarily used to place hair follicles collected from any animal species that has visible follicles. To place hair follicles, the two outer flaps are opened initially to expose the inner part. The touch cut on the base sheet on the inside part allows the outer plastic to be slowly peeled towards the crease of the outer cover thus exposing the low tack adhesive. The clear plastic sheet is easily pulled back due to the touch cut and the thicker lower base sheet (that is now stuck on the peeled plastic) acts as a good grip on the outer clear plastic. See FIG. 3 for a clear picture of this. It shows the inner device where the outer plastic is being peeled from the base sheet and this is done very easily due to the low tack adhesive that holds the clear plastic on the lower base. This is again useful for field uses as most samples from animals are collected in the field. Hair samples with follicles are placed within the peeled off area with the follicles all clumped together and this can be in any direction that is convenient to the user. The peeled back clear plastic is placed back on the hair samples, pressed firmly down with fingers and the two outer flaps are closed by inserting the tab into the lower outer flap slit. Any excess hair is trimmed off if necessary. Relevant information about the sample can be indicated on the outer flaps along with the animal ID. The presence of a collection device ID (the barcode or any other number or ID system present on the device) allows linking of the sample to its collection device ID (for example barcode of the collection device) and vice-versa. Once in the device, the sample can be stored at room temperature for an indefinite period of time and allows the easy shipment of samples in a regular or padded envelope.

Isolation of DNA from Hair Follicles that are in the Collection Device

For isolating DNA or other nucleic acid from the hair follicles, the follicles can be removed one at a time or in groups if necessary so that each follicle can be cut out with a sharp device like scissors. The device is designed in such a way that allows for the laboratory technician to visibly inspect the hair follicles and determine which follicle to remove. Individual follicles can be removed by simply peeling the outer plastic cover using the touch cut grip. This is possible due to the low tack adhesive that is used in the device. Removal of the follicle can be accomplished by punching out the hair follicle from the internal part of the device that holds the hair, using a punching device (1.2 mm Harris Micro punch (Whatman Biosciences) or similar device). The follicles can be punched out through the outer clear plastic and the lower base. All the follicles can be punched out from a device or just the sufficient number to isolate DNA. Typically, 1 to 5 follicles are sufficient to generate enough genomic DNA so as to facilitate DNA analysis using amplification methods like PCR (polymerase chain reaction (Erlich, H. A. 1989.)). The clear plastic sheet or the base sheet as well as the adhesive can be selected so as to select materials that do not inhibit reactions like the polymerase chain reaction that is routinely used in several labs to allow amplification of DNA for further analysis.

What is claimed is:

1. A collection device for collecting biological samples comprising:
    (a) a top flap;
    (b) a bottom flap coupled to the top flap at a seam; and
    (c) an inner device disposed between the top flap and the bottom flap and coupled to one or both of the top flap and the bottom flap at a region proximate to the seam, the inner device comprising a base and a top sheet, the top sheet being fixedly coupled to the base at a region proximate to the seam and the top sheet being partially separably coupled to the base at a region comprising substantially all of an area of overlap of the base by the top sheet and extending away from the seam;
    wherein:
    (i) the top sheet is partially separably coupled to the base by an adhesive extending over substantially all of the area of overlap of the base by the top sheet,
    (ii) the top sheet comprises a grip extending in a direction distal to the seam,
    (iii) the grip is positioned at a distal end of the top sheet relative to the seam,
    (iv) the base comprises (A) a first portion proximal to the seam and fixedly coupled to the top sheet at the region proximate to the seam and (B) a second portion distal to the seam and separated from the first portion of the base, (v) the grip comprises the second portion of the base coupled to the top sheet by the adhesive at the distal end of the top sheet relative to the seam, and (vi) the top sheet and base are configured to be punched out to provide portions of the top sheet and the base with a portion of the biological sample disposed therebetween.

2. The collection device of claim 1, wherein the top sheet comprises a clear plastic.

3. The collection device of claim 2, wherein the base comprises a plastic that is more rigid than the clear plastic of the top sheet.

4. The collection device of claim 1, wherein the base comprises paper.

5. The collection device of claim 1, wherein the biological sample is an animal sample.

6. The collection device of claim 1, wherein the inner device is coupled to one or both of the top flap and the bottom flap by an adhesive.

7. The collection device of claim 1, wherein an outer surface of one or both of the top flap and bottom flap comprises a unique identifier for the collection device.

8. The collection device of claim 7, wherein the unique identifier comprises a machine readable barcode.

9. The collection device of claim 1, further comprising a hair follicle sample fixed by the adhesive in the inner device between and in contact with both the base and the top sheet of the inner device.

10. The collection device of claim 1, wherein:
    (i) the inner device is coupled to the top flap and the bottom flap; and
    (ii) the top sheet cannot be completely removed from the base sheet.

11. The collection device of claim 1, wherein the collection device comprises only a single inner device between the top flap and the bottom flap.

* * * * *